United States Patent [19]

Murao

[11] 4,010,258
[45] Mar. 1, 1977

[54] MICROBIAL AMYLASE INHIBITOR AND PREPARATION THEREOF WITH THE USE OF STREPTOMYCES DIASTICUS VAR. AMYLOSTATICUS

[75] Inventor: Sawao Murao, Sakai, Japan

[73] Assignees: Ajinomoto Co., Inc.; Eisai Co., Ltd., both of Tokyo, Japan

[22] Filed: Mar. 12, 1975

[21] Appl. No.: 557,555

[30] Foreign Application Priority Data

Mar. 15, 1974 Japan .............................. 49-29646
Mar. 15, 1974 Japan .............................. 49-29647

[52] U.S. Cl. .................................. 424/115; 195/101
[51] Int. Cl.² ...................... A61K 35/00; G07F 3/02
[58] Field of Search ............. 424/115; 195/99, 100, 195/80 R, 101

[56] References Cited

UNITED STATES PATENTS

| | | | |
|---|---|---|---|
| 3,806,421 | 4/1974 | Ueda et al. ..................... | 195/80 R |
| 3,855,066 | 12/1974 | Frommer et al. ................ | 195/80 R |
| 3,876,766 | 4/1975 | Frommer et al. ................ | 424/115 |
| 3,879,546 | 4/1975 | Frommer et al. ................ | 424/115 |

*Primary Examiner*—Albert T. Meyers
*Assistant Examiner*—Daren M. Stephens
*Attorney, Agent, or Firm*—Frank J. Jordan

[57] ABSTRACT

A new amylase inhibitor, called Amylostatin-A, which can be distinguished from those disclosed heretofore on the basis of its constitution, molecular weight, specificity for certain types of amylase and adsorbability, is obtained by cultivating a strain of actinomycetes belonging to *Streptomyces diastaticus var. amylostaticus* FERM P-2499 in a medium containing starch, preferably amylopectin, as the sole source of carbon; the conditions of cultivation, methods of isolation and purification and therapeutical application thereof are disclosed.

15 Claims, 4 Drawing Figures

FIG. 2

MICROBIAL AMYLASE INHIBITOR AND PREPARATION THEREOF WITH THE USE OF STREPTOMYCES DIASTICUS VAR. AMYLOSTATICUS

BACKGROUND OF THE INVENTION

1. Field of the Invention

This invention relates to a new amylase inhibitor called Amylostatin-A and also it relates to its production by fermentation, as well as to methods for recovery and purification thereof. It also embraces therapeutical applications thereof for the regulation of lipid metabolism disorders.

2. Description of the Prior Art

Amylase inhibitors are known to be useful as biochemical reagents for various biological experiments and chemical assays and as therapeutical medicines for corpulence.

Since an amylase inhibitor was found in germinated buckwheat, it has been investigated in wheat, rye, sorghums and resting potato tubers although its production by microorganisms has been only limitedly reported.

Heretofore, Nojirimycin which is a kind of amino sugar and has been recently reported by T. Niwa et al (*Agr. Biol. Chem.*, 34. 966 (1970) ) and a peptide-like substance which has been reported by S. Ueda et al (*Agr. Biol. Chem.*, 37, 2025 (1973) ) are the only known amylase inhibitors produced from microbial sources. These two substances with antibiotic properties have been obtained from the cultured broth of certain species of Streptomyces. However, both production yields and amylase inhibitory activities thereof are extremely low and not suitable for industrial purposes.

SUMMARY OF THE INVENTION

According to the present invention, it has been discovered that a certain strain of actinomycetes belonging to a new variety of *Streptomyces diastaticus* produces a new, highly effective amylase inhibitor which is accumulated in the cultured broth thereof. This amylase inhibitor is unique in its chemical constitution, molecular weight, specificity for certain amylases and other physiochemical properties which differ from those of amylase inhibitors disclosed heretofore.

Therefore, it is an object of the present invention to provide a new amylase inhibitor, called Amylostatin-A, from microbial sources.

Another object of the invention is to provide a process for producing the aforementioned inhibitor by fermentation.

A further object of the invention is to provide a process for isolating and purifying the aforementioned inhibitor from cultured broth thereof.

A still further object of the invention is to provide a therapeutical application of the aforementioned inhibitor for lipid-metabolism disorders.

DETAILED DESCRIPTION OF PREFERRED EMBODIMENT

An example of the microorganism employed herein is a new variety of *Streptomyces diastaticus*, *Streptomyces diastaticus* var. *amylostaticus* FERM P-2499, although other strains capable of producing amylase inhibitors can be used.

Comparing the microbiological characteristics of the aforementioned new variety of *Streptomyces diastaticus* with those of known species of *Streptomyces* which have similar characteristics and have been described in the memoir of the *International Streptomyces Project*, ISP, the morphological and physiological properties of the new variety do not completely coincide with those properties of any one known species, as shown in Table 1.

Table 1

Comparative Table of Morphological and Physiological Properties of Known Species and the Present Strain

| species name (literature) | spore-chains[*1] morphology (of aerical mycelium) | (No. 1) spore surface | color of[*2] colony | pigmentation[*1] of substrate mycelium (reverse side) | soluble[*1] pigment |
|---|---|---|---|---|---|
| the present strain | spirales | smooth (warty) | G B R | 0~B | Mel± Y—B |
| St. murinus (1) | spirales | smooth (warty) | G G-B | G-Y-R | Mel- Y |
| St. nigrifaciens (1) | Rect. | smooth | G | ND | Mel- Y~0 |
| St. endus (2) | spirales | warty | G (hygroscopic) moist black | ND | Mel- colorless |
| St. scabies (2) | Rect. | smooth | G | Y~B | Mel- Y~GY |
| St. albidoflavus (3) | Rect. (w.d.) | smooth | W-G | ND | Mel- colorless |
| St. flavogriseus (3) | Rect. | smooth | G | Y~OY | Mel- Y± |
| St. lucenis | | hairy | | | Mel+ |

Table 1-continued

| | | | | | |
|---|---|---|---|---|---|
| (3) St. | spirales | spiny | G | ND | colorless |
| noboritoensis (3) | Rect. | smooth | G (w.d.) G | Y~B | Mel+ B |
| St. alni (4) | Rect. (p.d.) | smooth | W Y | ND | Mel- Y |
| St. capoamus (4) | Reti-ap. | R | G (pH ind) | R Y~O | Mel- |
| St. diastaticus (4) | spirales | smooth | G Y | ND | Mel- colorless |
| St. griseoluteus (4) | Rect. (sclerotic) | smooth | G (R,W) | ND | Mel- R~Blue (pH ind) |
| St. spadicis (4) | Rect. | smooth | G | O G~O (pH ind) | Mel+ colorless |
| St. willmorei (4) | Rect. | smooth | G Y W | ND | Mel- Y± |

| species name (literature) | L-arabi-nose | D-xy-lose | D-glu-cose | (No. 2) D-fruc-tose | D-rham-nose | suc-rose | raffi-nose | D-manni-tol | Inositol |
|---|---|---|---|---|---|---|---|---|---|
| the present strain | + | + | + | + | − | ± | ± | + | − |
| St. murinus(1) | − | + | + | + | − | − | − | + | Var |
| St. nigrifaciens (1) | + | + | + | Var | + | − | − | + | − |
| St. endus(2) | + | + | + | + | + | − | − | + | − |
| St. scabies(2) | + | + | + | + | + | − | − | + | − |
| St. albidoflavus (3) | + | + | + | + | − | − | − | + | − |
| St. flavogriseus (3) | + | + | + | + | + | − | − | + | − |
| St. lucensis (3) | + | + | + | + | − | + | − | + | − |
| St. noboritoensis (3) | + | + | + | + | − | ? | + | + | Var |
| St. alni(4) | + | + | + | + | ? | ? | ? | + | ? |
| St. capoamus (4) | + | + | + | + | − | − | ? | + | − |
| St. diastaticus (4) | + | + | + | + | − | + | − | + | − |
| St. griseoluteus (4) | + | + | + | + | − | − | − | + | − |
| St. spadicis (4) | + | + | + | + | Var | − | Var | + | Var |
| St. willmorei (4) | ? | + | + | + | + | − | − | + | − |

Note
(1) ISP Int. J. Syst. Bact. 18, 69 (1968)
(2) ISP Int. J. Syst. Bact. 18, 279 (1968)
(3) ISP Int. J. Syst. Bact. 19, 391 (1969)
(4) ISP Int. J. Syst. Bact. 22, 265 (1972)
*¹Rect.: Rectiflexibiles, meaning that sporophores (spore chains) are straight to flexuous.
Reti.-ap.: Retinaculi-aperti, indicating spore chain morphology intermediate of spirales and rectiflexibiles, that is, open loops, hooks of wide diameter or spirals of wide diameter.
*²G: grey B: brown R: red W: white Y: Yellow O: orange ND: not distinctive pH ind: pH indication Mel: melanoids w.d.: aerial mycelium weakly developed p.d.: aerial mycelium poorly developed hygroscopic: moist, black
*³Var: variable Furthermore, comparisons have been made between the strains of *Streptomyces* which are described in *The Actinomycetes*, Vol. II, by S. A. Waksman (1961) and the present strain with respect to hydrolytic activity on starch, gelatin and milk as shown in Table 2.

Table 2. Table of Comparative Hydrolytic Activites of Known Species and the Present Strain

| | | | hydrolytic activities on milk | |
|---|---|---|---|---|
| species name | starch | gelatin | poptonization | coagulation |
| the present strain | + | ± | + | + |
| St. murinus | − | ± | ? | ? |
| St. nigrifaciens | ± | ± | ± | + |
| St. endus | ++ | ± | | |
| St. scabies | + | ± | ± | ± |
| St. flavogriseus | + | ± | ++ | |
| St. lusensis | + | − | | |
| St. noboritoonsis | − | ± | | |
| St. diastaticus | ++ | + | ± | + |
| St. griseoluteus | + | no growth | | |
| St. willmorei | | + | ± | + |

Descriptions of the Streptomycetes other than that of the present invention are in *The Actinomycetes*, Vol II, by S. A. Waksman (1961).

Among known species the present strain is very similar to *Streptomyces murinus*, *St. lucensis*, *St. noboritoensis* and *St. diastaticus* in cultural and physiological characteristics. However, the present strain can be distinguished from those species in the following morphological and physiological properties. All the descriptive characteristics hereinafter are the result of cultivation on the usual ISP medium unless otherwise mentioned.

*St. murinus* can neither assimilate arabinose nor hydrolyze starch.

The surface of the spores of *St. lucenis* are clearly different morphologically in that they are hairy or spiny and *St. lucenis* does not produce a distinctive soluble pigment.

*St. noboritoensis* does not exhibit a perfect spiral in spore chains of aerial mycelium and cannot hydrolyze starch.

Thus, *St. diastaticus* is most closely related to the present strain, though it is not completely identical because it does not produce soluble pigment and has no distinctive pigment in the substrate mycelium. However, these small differences are insufficient to identify this strain as a different species from *St. diastaticus*.

Therefore, the present strain should be identified as a variety of *St. diastaticus*. This strain has been designated as *St. diastaticus var. amylostaticus* FERM P-2499 and has been deposited in the Fermentation Research Institute of Japan and added to its permanent collection of microorganisms as FERM No. 2499 and is freely available from the Institute by taking the necessary steps to acquire it.

Variation and mutation of the present strain is naturally expected since such is a common property of an actinomycetes. *St. diastaticus var. amylostaticus* FERM P-2499 includes the typical strain described above and all natural and artificial variants and mutants thereof. That is, by this definition, *St. diastaticus var. amylostaticus* of the present invention includes all strains producing Amylostatin-A except those producing Amylostatin-A which can be absolutely differentiated therefrom.

Hereinafter, the amylase inhibitor in accordance with this invention refers to Amylostatin-A, which will be subsequently described in detail.

The process for the production of the present amylase inhibitor, Amylostatin-A, comprises cultivating a strain belonging to the above described *St. diastaticus var. amylostaticus* in a medium containing an assimilable carbon source, nitrogenous nutrient and inorganic salts which are conventionally used.

Among the known sources of carbon, a medium containing starch is preferable. Especially, the accumulation of Amylostatin-A can be greatly increased by employing amylopectin as a source of carbon whereas a medium containing glucose as the main source of carbon markedly decreased the accumulation of Amylostatin-A.

Conventional sources of nitrogen, such as peptones, meat extract, yeast extract, hydrolysed defatted soybean meal and the like can be used.

The use of inorganic ammonium salts and minor nutritional ingredients such as vitamins is necessary for some strains. Any other kinds of constituents which can be utilized by Amylostatin-A producing organisms for the production of Amylostatin-A are useful even if they are not mentioned in this specification.

After the pH of the culture medium consisting of the above constituents in appropriate amounts is adjusted to an approximately neutral pH and the culture medium is sterilized and inoculated with the inoculum of organisms according to the invention, cultivation is carried out aerobically at 20°–40° C. for 1 – 4 days in a conventional shaker or tank for submerged culture until the above organism grows favorably, producing Amylostatin-A and has substantially accumulated it in the cultured broth.

For the isolation of Amylostatin-A, a combination of conventional methods such as adsorption on active carbon, chromatography, gel filtration with Sephadex and fractional precipitation with solvents such as acetone can be employed. In addition, those purification methods which utilize the formation of the enzyme inhibitor complex, that is the amylase-Amylostatin-A complex, are preferable. The complex can be easily prepared by placing Amylostatin-A in contact with amylase in a buffered or unbuffered solution of pH 3 – 9, preferably with stirring and heating slightly in order to accelerate the reaction rate. To isolate the thus obtained complex from other foreign substances, conventional molecular fractionation such as Sephadex (Pharmacia A.B.) gel filtration, dialysis and ultrafiltration can be employed. Alternatively to placing Amylostatin-A in contact with amylase, adsorption of the Amylostatin-A on immobilized amylase which has been fixed previously by a conventional method can be utilized.

For example, a solution containing the complex of amylase-Amylostatin-A is applied to a Sephadex column for gel filtration and is collected in purified fractions. After breaking down the thus purified complex into the original components, amylase and Amylostatin-A, the resulting solution is again applied to a Sephadex column for gel filtration to collect the active fractions. Thus, the purified amylase inhibitor can be easily obtained since foreign substances having similar molecular weights have been removed in the preceding gel filtration.

In order to break down the complex into its components, it is sufficient to place the complex in contact with an aqueous solution of a protein denaturing agent such as urea and urea derivatives, for example, urea, thiourea, iminourea, N-methylurea and the like, in which the concentration of the agent is more than 4 M/l of aqueous solution and which will accelerate the breaking-down rate.

Merely adjusting the pH of the solution containing the complex to a maximum alkaline of acidic range which will keep the amylase active cannot completely break down the complex into its components.

To recover the inhibitor, Amylostatin-A, from the above mixture, a conventional molecular fractionation method is employed, as mentioned above. For example, after adjusting the pH of the mixture, it may be placed on a Sephadex column for gel filtration in which elution is carried out with water. Amylase contained in the mixture can be reused repeatedly according to the procedure which comprises recovering the amylase as one of the products from the break-down reaction and allowing it to stand overnight at room temperature in water or a buffer solution in order that it be reactivated.

According to the procedure of the present invention, remarkably pure Amylostatin-A is obtained which has a specific activity that is 100 to 200 times greater than that obtained by conventional procedures.

Alternatively, a solution of Amylostatin-A, containing ionic impurities is placed on a column of ion-exchange resin; ionic impurities are removed by being adsorbed onto the resin whereas Amylostatin-A passes down through it without being adsorbed; therefore, the purity of Amylostatin-A can be increased still further. In this procedure, strongly acidic cation-exchange resin (DOWEX 50w) or strongly basic anion-exchange resin (DOWEX 1) is used in the range of pH 1 to 14.

By way of example, centrifugation, filtration and other ordinary methods are used to remove the mycelium from the fermented broth and active carbon is added to the supernatant solution and mixed to adsorb the Amylostatin-A. Then, after separating the active carbon from the solution, elution is carried out with aqueous ethanol of 10 to 90% by volume ethanol concentration, although a 60% by volume solution is preferred. (In this specification % indicates the percent calculated using ordinary weight by volume measurements unless otherwise described.)

The eluate is concentrated in vacuo and freeze dried, yielding the active inhibitor as a white powder having 75 – 80% of the total activity which existed in the cultured broth.

Assay of amylase activity:

The reaction mixture consisting of 4 ml of a 1.5% soluble starch solution in 0.1M acetate buffer solution at pH 5.5, 0.5 ml of distilled water and 0.5 ml of the amylase solution to be assayed (amylase or bacterial α-amylase (crystalline) ) is incubated at 37° C. for 10 minutes and the reaction is terminated by adding a mixture of 5:1 by volume of 0.5N acetic acid and 0.5N hydrochloric acid. From this solution, 0.2 ml is withdrawn and added to 5 ml of N/3000 iodine solution and the absorbency is measured at 660 nm. The amylase activity per one ml of the enzyme solution expressed in units is calculated as follows:

$$600 \times \frac{D_o - D}{D} \text{ units}$$

in which D is the optical density of the enzyme solution and $D_o$ is the optical density of the control.

Assay of amylase inhibitory activity:

The reaction mixture consisting of 0.5 ml of 2 × $10^{-4}$% of bacterial α-amylase (crystalline) and 0.5 ml of the solution of Amylostatin-A is incubated at 37° C. for 10 minutes. Any residual amylase activity is determined according to the method of assay of amylase activity described above. One unit of amylase inhibitory activity is defined as the amount of inhibitory activity necessary to inactivate one unit of amylase.

The Amylostatin-A preparation obtained from the cultured broth according to Example 1 described hereinafter was demonstrated to be a new amylase inhibitory agent possessing the following physicochemical and physiological properties:

1. Amylase inhibitory action on various kinds of amylase

The degree of amylase inhibitory activity of Amylostatin-A on amylase obtain from different sources is shown in Table 3.

Table 3

| kind of amylase | sources | intensity |
| --- | --- | --- |
| α-amylase | Bacillus stearothermophilus | + |
| | bacterial liquefying amylase | + |
| | bacterial saccharogenic amylase | + |
| | Taka-amylase A | + |
| | Aspergillus niger | + |

Table 3-continued

| kind of amylase | sources | intensity |
| --- | --- | --- |
| | (stable at acidic pH) Aspergillus niger | + |
| | (unstable at acidic pH) malt amylase | + |
| | salivary amylase | + |
| | pancreatic (swine) amylase | + |
| β-amylase | wheat amylase | − |
| | soya bean amylase | − |
| glucoamylase | Rhizopus niveus | + |
| iso-amylase | Aerobacter aerogenes | − |

Note:
The notation + indicates that the percentage of residual amylase activity is not more than 50, and − indicate that it is more than 50.

All samples of amylase were in the crystalline form and Amylostatin-A was the purified preparation. The assay of inhibitory activity was performed using the aforementioned method of determination.

The degree of amylase inhibitory activity on amylase mentioned here corresponds to substrate specificity in enzymology. But substrate specifcity is terminology indicating the relationship of enzyme to substrate whereas specificity here indicates the relationship of inhibitor to enzyme.

As shown in Table 3, the inhibitor of this invention has specificity for α-amylase and glucoamylase but cannot inhibit β-amylase and isoamylase.

2. Action of various proteases on Amylostatin-A

Proteases such as trypsin, chymotrypsin, papain and pepsin have been demonstrated to be unable to inactivate the inhibitory activity of Amylostatin-A on amylase.

3. Stability

Amylostatin-A has substantial stability when it is held in a buffer solution at a pH ranging from 1 to 12 at 37° C. for 12 hours and also when it is heated at 100° C. for 30 minutes in the same range of pH.

4. Infrared absorption spectrum

Figure 1:
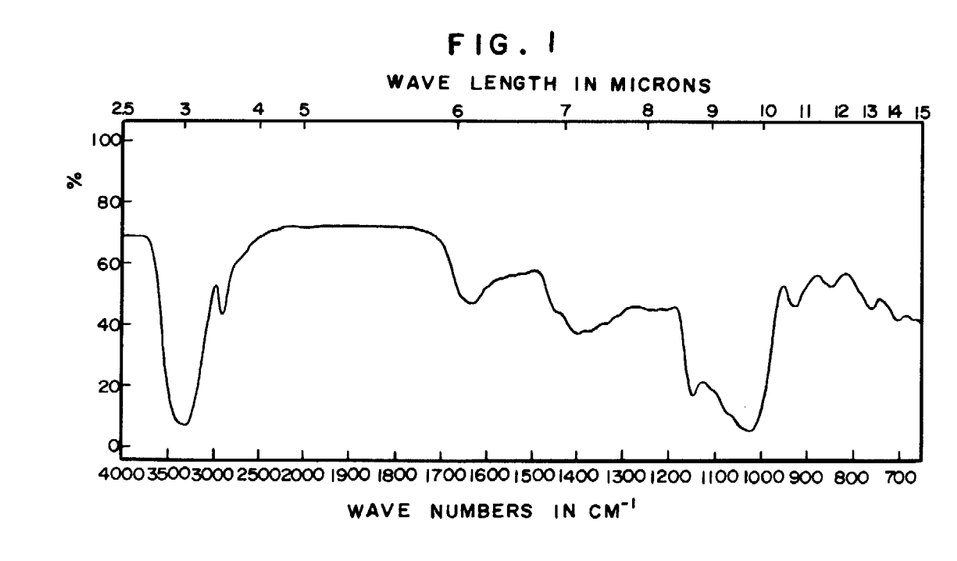
FIG. 1 shows the infrared adsorption spectrum (KBr) of Amylostatin-A in accordance with the present invention.

Amylostatin-A exhibits characteristic absorption bands in the infrared region of the spectrum when pelleted with potassium bromide, as shown in FIG. 1.

5. Elementary analysis

Elementary analysis of Amylostatin-A shows the following:

Found: C, 39.94; H, 6.76; N, Less than 1%.

On the basis of the results of hydrolysis in which the products were mainly glucose, it is concluded Amylostatin-A is a kind of oligo-saccharide, poly-saccharide, or derivative thereof.

6. Molecular weight

When the purified Amylostatin-A is applied to calibrated columns of Sephadex-50 for gel filtration, Amylostatin-A activity is eluted as a single symmetrical peak and the apparent molecular weight of Amylostatin-A is calculated to be around 2000 by employing reference proteins.

7. Solubility

Amylostatin-A is soluble in water and pyridine and substantially insoluble in methanol, ethanol, chloroform and acetone.

8. Adsorbability

Amylostatin-A is adsorbed on active carbon at a pH range of 1 to 12, but it is not adsorbed onto a column of ion-exchange resin and flows down through the column along with the aqueous solution passing through the column. The ion-exchange resin herein used and the conditions of use thereof are similar to that described above.

Thus, comparing such properties of Amylostatin-A as described above with those of microbial amylase inhibitors which have been reported heretofore, it is concluded Nojirimycin reported by Niwa et al (*Agr. Biol. Chem.* Vol. 34, No. 6 p. 966–968 (1970) ) is a kind of 5-amino sugar whereas Amylostatin-A is a kind of saccharide and the respective molecular weights are clearly different. Therefore Amylostatin-A is a different substance from the Nojirimycin.

Furthermore the amylase inhibitor reported by Ueda et al (*Agr. Biol. Chem.*, Vol. 37, No. 9 p. 2025 – 2030, (1973) ) is a peptide-like substance which contains certain sugars and its adsorbability on a column of ion-exchange resin is clearly different from that of Amylostatin-A, proving that Amylostatin-A is also a different substance from the inhibitor reported by Ueda and, accordingly, appropriately given a different name.

Biological test on digestibility of starch:

An experiment concerning the inhibitory effect of Amylostatin-A on the digestion and absorption of starch in vivo was carried out using sound male rats of Wistar strain weighing from 250 to 300g. After they had been made to fast, receiving only water for 48 hours, 60 rats were selected and divided into 10 groups of each 5 or 10 as shown in Table 4.

Table 4

| kind of starch | amount of Amylostatin-A added (mg) | time lapse (hour) | number of rats | residual % of starch (average) (%) |
|---|---|---|---|---|
| | | 1 | 5 | 61.8 |
| | | 2 | 10 | 55.9 |
| | 0 | 3 | 5 | 44.0 |
| | | 4 | 10 | 45.4 |
| cornstarch | 10 | 4 | 5 | 92.5 |
| | 5 | 4 | 5 | 93.6 |
| | 2.5 | 4 | 5 | 82.5 |
| | 0 | 4 | 5 | 10.5 |
| soluble starch (dissolved) | 10 | 4 | 5 | 65.7 |
| on heating) | 5 | 4 | 5 | 63.8 |

Rats in control groups were given either 2.5 ml of an isotonic sodium chloride solution in which 300 mg of soluble starch (Wako Junyaku Co., Inc.) was dissolved or 2.5 ml of an isotonic sodium chloride solution in which 300 mg of corn starch (Japanese Pharmacopia) was suspended. The rats were subjected to a laparotomy, the solution was injected into the stomach and the incision site was sutured. Rats in test groups were given the same amount and kinds of solutions as given to the rats in control groups except that varying amounts of crude Amylostatin-A obtained according to the methods of Example 1 were added as shown in Table 4. The test solutions were administered in the same manner as the control solutions.

After the lapse of definite periods of time, all rats were again laparotomized at the site of the original incision and all contents of the stomach and small intestines were removed by washing with an isotonic sodium chloride solution. To these washings containing residual starch, 25 ml of 1N hydrochloric acid was added. The mixture was heated to carry the hydrolytic reaction to completion and the quantity of reducing sugar formed was determined by Somogyi's method. The amount of residual starch which had not been absorbed was calculated therefrom and is shown in Table 4.

The results of Table 4 show that administering more than 2.5 mg of crude Amylostatin-A per animal could distinctly suppress the digestion and absorption of soluble starch as well as uncooked corn starch. This fact strongly suggests that Amylostatin-A has a marked effect on disorders of metabolism which are commonly found in human beings who ingest large amounts of gelatinized starch.

In accordance with the invention, humans and animals having, carbohydrate metabolism disorders may be chemotherapeutically treated by oral administration of the amylase inhibitor of the invention in a dosage sufficient to mitigate the disorders or symptoms without causing toxicity. Consequently, another aspect of the invention is a pharmaceutical composition for oral administration to humans and animals comprising the amylase inhibitor of the invention in combination with a pharmaceutically acceptable non-toxic carrier.

The compositions of the invention may be presented for administration in the form of tablets, pills, capsules, powders, granules, solutions or suspensions and the like. For preparing solid compositions such as tablets, the principal active ingredient is mixed with conventional tableting ingredients such as corn starch, lactose, sucrose, sorbitol, talc, stearic acid, magnesium stearate, dicalcium phosphate, gums, and functionally similar materials as pharamceutical diluents or carriers. The tablets or pills of the novel composition can be laminated or otherwise compounded to provide a dosage form affording the advantage of prolonged or delayed action or predetermined successive action of the enclosed medication. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate, and the like. A particularly advantageous enteric coating comprises a styrenemaleic acid copolymer together with known materials contributing to the enteric properties of the coating.

The liquid forms in which the novel composition of the present invention may be incorporated for administration include aqueous solutions, suitably flavored syrups, aqueous or oil suspensions, flavored emulsions with edible oils such as cottonseed oil, sesame oil, coconut oil, peanut oil and the like, as well as elixirs and similar pharmaceutical vehicles. Suitable dispersing or suspending agents for aqueous suspensions include synthetic and natural gums such as tragacanth, acacia, alginate, dextran, sodium carboxmethylcellulose, methylcellulose, polyvinylpyrrolidone, gelatin and the like.

EXAMPLE 1

Several 100 ml portions of a medium of pH 7.0 consisting of

| meat extract | 0.5 g/dl, |
| peptone | 0.5 g/dl, |

| | |
|---|---|
| sodium chloride | 0.3 g/dl, and |
| soluble starch | 2 g/dl | were incorporated in a 500 ml flask for a shaking culture, sterilized at 120° C. for 10 minutes, and inoculated with 2 ml of an inoculum of St. diastaticus var. amylostaticus FERM P-2499 which had been previously cultured at 30° C. for 24 hours in an identical medium.

The fermentation was carried out at 30° C. for 48 hours with shaking. The resultant cultured broth was centrifuged to separate the mycelia and the amylase inhibitory activity of the supernatant was 4000 units/ml.

The supernatant portions of eight identical cultures were combined, giving 740 ml of cultured broth with an amylase inhibitory activity of 3500 units/ml. To this cultured broth, 30 g of active carbon was added. The carbon was suspended in the cultured broth, filtered out, washed sufficiently with water and re-suspended in 300 ml of deionized water. The pH of the suspension was adjusted to 11 and the suspensions was heated for 30 minutes at 80° C. and filtered. The thus obtained active carbon was washed with water repeatedly and subsequently with an aqueous solution of 0.005N hydrochloric acid and eluted with 750 ml of aqueous ethanol 60% by volume ethanol concentration. The eluate was concentrated in vacuo and the concentrated solution was freeze dried to give 7.1 g of white powder constituted of crude Amylostatin-A, which had an amylase inhibitory activity of 1 unit/3.54 mcg (yield 78%). The powder was dissolved in distilled water in a concentration of 5% by weight. Three volumes of acetone was added to this solution and the thus produced precipitate was harvested by centrifugation and then dissolved in distilled water and the resulting solution was made up to the original volume. To this solution was added 600 ml of 0.2M acetate buffer solution (pH 5.5) containing 10 mg/3 ml of of liquifying amylase from bacterial sources and a $CaCl_2$ solution of sufficient strength to result in a final concentration of 0.1M $CaCl_2$. The mixture was kept at 37° C. for 60 minutes to produce the amylase-Amylostatin-A complex.

This mixture containing the complex was applied to a Sephadex G-50 (Pharmacia A.B.) column (2.5 × 34 cm ) which had been equilibrated with 0.5M acetate buffer (pH 5.5) and column chromatography was performed by elution with the same buffer solution in 5 ml fractions with collection of the fractions of amylase-Amylostatin-A complex (fractions No. 15 to No. 25).

Figure 2:
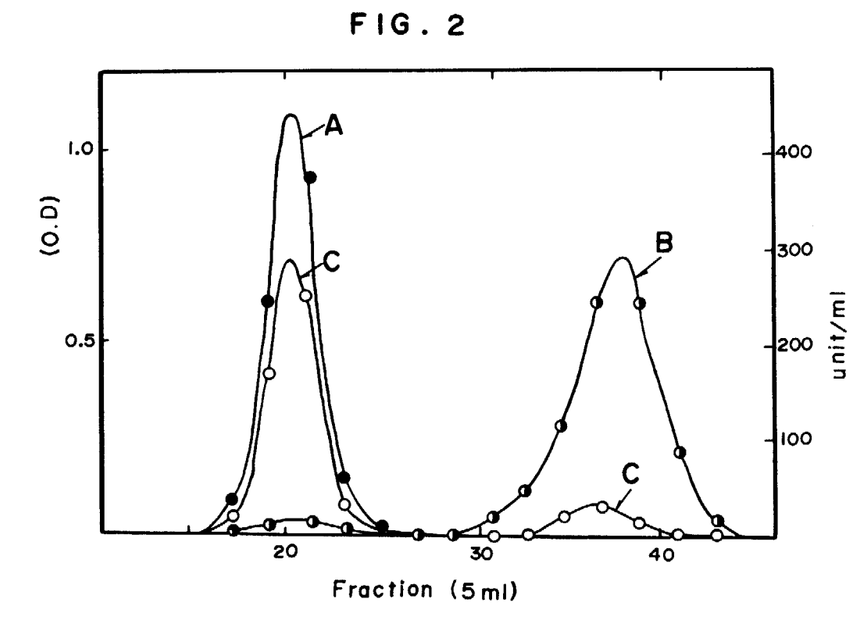
FIG. 2 shows a column chromatogram using Sephadex G-50 of the amylase-Amylostatin-A complex.
Figure 3:
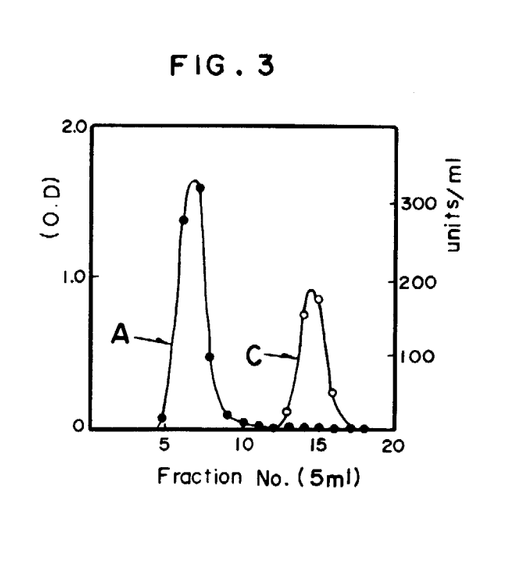
FIG. 3 shows the chromatogram of the break-down products of the complex; the break-down was accomplished by using urea.

This chromatogram is shown in FIG. 2, in which the optical density of curve A is measured at 280 nm and that of curve B at 490 nm and curve C indicates the inhibitory activity expressed in units/ml. The active fractions of amylase-Amylostatin-A complex, fractions 15 to 25, were pooled and two volumes of cold acetone were added thereto with cooling in order to precipitate the complex. The precipitate was harvested by centrifugation and then dissolved in distilled water. Sufficient urea was added to give a final concentration of 8M of urea, then the pH of the solution was adjusted to 2.5 and the solution was then allowed to stand overnight at room temperature to completely denature the amylase. The solution was then applied to a Sephadex G-50 column (2.5 × 15 cm) which had been equilibrated with 0.02M tris-HCl buffer at pH 8.5 and column chromatography was performed by eluting with the same buffer solution.

Thus, the fraction containing the inhibitor was eluted as a different fraction from that of amylase and urea could be easily separated therefrom.

The chromatogram is shown in Table 3 in which curve A illustrates the absorbency at a wave length of 280 nm and curve C illustrates inhibitory activity expressed in units/ml.

The resulting amylase fractions were pooled and allowed to stand overnight at 30° C. permitting the amylase to be reactivated and to be used repeatedly.

Figure 4:
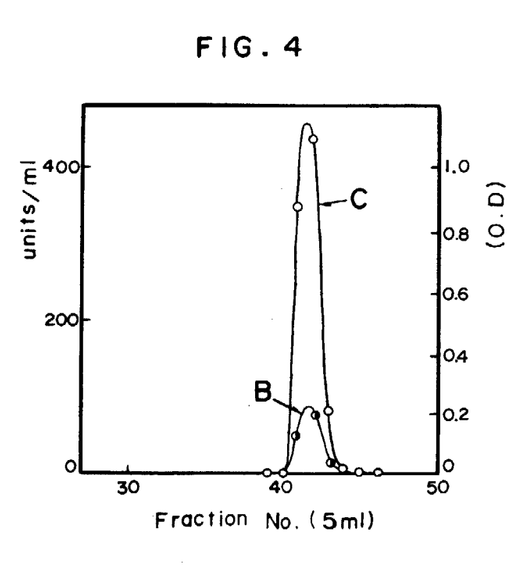
FIG. 4 shows the chromatogram of the aqueous eluate of the active fraction the chromatogram of which is shown in FIG. 3.

The fractions of the inhibitory substance, Amylostatin-A, were pooled and concentrated in vacuo and applied to a Sephadex G-50 column (25 × 30 cm) which had been equilibrated with distilled water and gel filtration was performed. The chromatogram is shown in FIG. 4 in which curve B indicates the adsorbency at a 490 nm wave length and curve C indicates the inhibitory activity expressed in units/ml.

The active fractions of the inhibitor were pooled and freeze dried to give a purified powdery preparation of Amylostatin-A at a yield of 30 mg per liter of cultured broth. The amylase inhibitory activity of this purified Amylostatin-A was $3.5 \times 10^4$ units per mg and the yield when compared to the activity of the cultured broth was calculated to be 30%.

EXAMPLE 2

The strain belonging to St. diastaticus var. amylostaticus FERM P-2499 was cultivated under the same condition as Example 1 with the only change being that amylopectin instead of soluble starch was employed as the sole source of carbon.

Identical methods were used as in Example 1 and the supernatant cultured broth was found to have an inhibitory activity of 7500 units/ml.

What is claimed is:

1. A process for producing an amylase inhibitor, Amylostatin-A, of claim 2 which comprises aerobically cultivating Streptomyces diastaticus var. amylostaticus FERM P-2499 in a medium containing an assimilable carbon source, nitrogenous material and inorganic salts, accumulating an effective amount of Amylostatin-A in the broth, and recovering the accumulated Amylostatin-A.

2. An amylase inhibitor, Amylostatin-A, prepared by the process of claim 1 having an oligo- or poly-saccharide constitution and characterized by the following physicochemical and biological properties:
   a. having a specific activity on certain amylases; the capability of inactivating α-amylase and glucoamylase, but the incapability of inhibiting β-amylase and isoamylase,
   b. being stable at room temperature as well as being heat resistant at a range of pH from 1 to 12,
   c. having an infrared absorption spectrum when pelleted with potassium bromide exhibiting the absorption band shown in appended FIG. 1,
   d. having an apparent molecular weight of about 2000 calculated on the basis of gel filtration and employing reference proteins,
   e. being soluble in water and pyridine but substantially insoluble in methanol, ethanol, chloroform and acetone,
   f. having adsorbability on active carbon in a pH range of 1 to 12 but in aqueous solution of pH 1 to 14 not being adsorbed on strongly acidic and strongly basis ion-exchange resins.

3. A process in accordance with claim 1 in which the assimilable carbon source is starch.

4. A process in accordance with claim 1 in which the assimilable carbon source is amylopectin.

5. A process in accordance with claim 1 in which Amylostatin-A is recovered from an aqueous solution thereof by adsorption on active carbon and is subsequently eluted with an aqueous solution of 10 to 90% by volume ethanol, and Amylostatin-A is recovered from the resultant eluate.

6. A process in accordance with claim 1 in which Amylostatin-A is recovered from an aqueous solution thereof by a combination of procedures comprising any of adsorption, chromatography, gel filtration and fractional precipitation with a solvent.

7. A process in accordance with claim 6 in which said solvent is at least one selected from the group consisting of methanol, ethanol, chloroform and acetone.

8. A process in accordance with claim 1 which comprises forming a complex of amylase and the amylase inhibitor, isolating said complex from foreign material, breaking down said isolated complex into a mixture of the original amylase and amylase inhibitor, and isolating said amylase inhibitor from said amylase.

9. A process in accordance with claim 8 in which both isolatings are performed by a combination of molecular fractionation procedures comprising any of gel filtration, dialysis and ultrafiltration and the breaking down is performed with a denaturing agent.

10. A process in accordance with claim 8 in which the amylase is repeatedly used to form a complex with the amylase inhibitor and each time is recovered from said mixture of amylase and amylase inhibitor after the break down of said complex.

11. A process in accordance with claim 8 in which the amylase is an immobilized amylase.

12. A process in accordance with claim 8 in which the breaking down is effected by contacting the complex with a denaturing agent selected from the group consisting of urea, thiourea, iminourea and N-methyl urea.

13. A pharmaceutical composition for oral administrations to humans and animals comprising an effective amount of the amylase inhibitor of claim 1 to regulate starch metabolism in combination with a pharmaceutically acceptable non-toxic carrier.

14. A method of treating living creatures of the group consisting of humans and animals to inhibit the digestion and absorption of starch ingested thereby which comprises orally administering to the human or animal the amylase inhibitor of claim 1 in a dosage sufficient to mitigate the disorder or symptom without causing toxicity.

15. A method according to claim 14 in which the living creatures are animals.

* * * * *